United States Patent [19]

Kligman

[11] Patent Number: 5,468,495
[45] Date of Patent: * Nov. 21, 1995

[54] METHODS OF PREVENTING AND REDUCING THE SIZE OF *STRIAE DISTENSAE* LESIONS

[76] Inventor: Albert M. Kligman, 210 W. Rittenhouse Sq., Philadelphia, Pa. 19103

[*] Notice: The portion of the term of this patent subsequent to Jul. 28, 2009, has been disclaimed.

[21] Appl. No.: 836,320

[22] PCT Filed: Aug. 30, 1990

[86] PCT No.: PCT/US90/04939

§ 371 Date: Mar. 6, 1992

§ 102(e) Date: Mar. 6, 1992

[87] PCT Pub. No.: WO91/03240

PCT Pub. Date: Mar. 21, 1991

Related U.S. Application Data

[63] Continuation-in-part of Ser. No. 402,271, Sep. 1, 1989, Pat. No. 5,134,163.

[51] Int. Cl.⁶ .............................. A61K 7/00; A61K 31/07
[52] U.S. Cl. .......................... 424/401; 514/559; 514/725
[58] Field of Search ........................... 424/401; 514/559, 514/725

[56] References Cited

U.S. PATENT DOCUMENTS

| | | | |
|---|---|---|---|
| 4,603,146 | 7/1986 | Kligman | 514/725 |
| 4,888,342 | 12/1989 | Kligman | 514/725 |
| 4,889,847 | 12/1989 | Kligman | 514/171 |
| 5,051,449 | 9/1991 | Kligman | 514/725 |
| 5,093,360 | 3/1992 | Yu et al. | 514/725 |
| 5,134,163 | 7/1992 | Kligman | 514/725 |

OTHER PUBLICATIONS

Schreuder, Johannes C. P., *Chemical Abstracts* 106:125892f (1987), p. 399.
Communication from Examiner, European Patent Office, Feb. 17, 1992, two pages.
Official Letter from National Bureau of Standards, Taiwan, Jan. 14, 1991 (English—translation—one page), Taiwan Patent Application No. 79107674.
Notification of Transmittal of International Preliminary Examination Report, International Applic. No. PCT/US90/04939, mailed Jul. 24, 1991, (7 pages).

*Primary Examiner*—John C. Bleutge
*Assistant Examiner*—Amy Hulina
*Attorney, Agent, or Firm*—Panitch Schwarze Jacobs & Nadel

[57] ABSTRACT

Striae distensae lesions may be prevented and/or reduced in size by topically applying to the skin affected with the lesions an effective amount of a retinoid, preferably retinoic acid, preferably by daily application in a dermatologically acceptable vehicle, such as a cream base, at a concentration of about 0.025 to 0.1 weight percent retinoic acid. When applied during the striae rubrae stage, the retinoid may be effective to prevent the formation of striae albae lesions, and when applied in either stage, the retinoid may be effective to reduce the width and depth of the lesions, with improved texture and softness.

8 Claims, No Drawings

METHODS OF PREVENTING AND REDUCING THE SIZE OF STRIAE DISTENSAE LESIONS

CROSS-REFERENCE TO RELATED APPLICATION

This application is a continuation-in-part of U.S. patent application Ser. No. 07/402,271, filed Sep. 1, 1989 now U.S. Pat. 5,134,163 and corresponds to PCT/US90/04939, filed Aug. 30, 1990, now International Publication No. WO 91/03240.

FIELD OF THE INVENTION

The present invention is directed to methods of preventing and/or reducing the size of lesions of striae distensae. More particularly, the invention is directed to a method of preventing the formation of stride albae and a method of reducing the size of lesions of both striae albae and striae rubrae.

BACKGROUND OF THE INVENTION

Striae distensae are very common lesions. They are present in most healthy adult women, having originated either during puberty or at the time of the first pregnancy. Stretching of the skin, as in rapid weight gain, or mechanical stress, as in weight lifting, often precedes their development. About 50 percent of pregnant women will develop these lesions, often referred to as stretch marks, on thighs, abdomen and breasts, starting at about 3 to 4 months of gestation. However, such lesions are also noted in cachectic states, for example in tuberculosis and typhoid fever, and they have also been noted after intense slimming diets.

The pathogenesis of stride distensae lesions is unclear. Some pregnant women do not develop the lesions; lesions have not been produced experimentally, and there is no animal model.

Clinicians are aware that striae distensae evolve over time passing through an early phase of inflammation (striae rubrae) and ending in the typical white stretch mark (striae albae). The striae rubrae are red, slightly elevated, linear lesions that may be tender. Later, the lesions flatten and the redness fades, leaving a permanent, wavy depression, which is the striae albae. The striae albae lesions may be 5 to 15 mm wide, depressed with a crinkly surface. These are the stretch marks which last for life, since to date there has been no known treatment.

The histopathology of striae, which always have the same appearance regardless of cause, has generated much dispute. However, P. Zheng, et al., "Anatomy of Striae," *British Journal of Dermatology*, 112:185–193 (1985) present evidence that striae albae are true scars resulting from an earlier inflammatory process that destroys elastic fibers. They are not formed by stress-induced rupture of the dermal fibrous network.

Retinoids, particularly retinoic acid, have been previously applied topically to the skin for the treatment of many skin disorders. See, for example the review of Thomas et al., "The Therapeutic Uses of Topical Vitamin A Acid," *Journal of the American Academy of Dermatology*, 4:505–513 (1981). It is known that tretinoin has an anti-inflammatory action useful in ameliorating chronic dermatoses such as psoriasis and lichen planus.

According to my U.S. Pat. Nos. 4,603,146; 4,877,805 and 4,888,342, topical retinoids have been effective to stimulate formation of new collagen fibers, generate new blood vessels, correct abnormalities in elastic fibers, and eliminate neoplastic growths in chronically sundamaged skin. Retinoic acid is used world-wide to retard and reverse photodamage from excessive exposure to ultra-violet radiation in sunlight.

The literature also reports the improvement of post-ache, elevated, hypertrophic scars of the back with topical retinoic acid. These hypertrophic scars have a very different origin, following severe cystic lesions, resulting in a high increase in collagen. In striae distensae the opposite happens; there is loss of collagen with atrophic scarring.

BRIEF SUMMARY OF THE INVENTION

According to the present invention, it has been found that striae distensae lesions may be prevented and reduced in size by applying a retinoid, preferably tretinoin, topically to the area of the skin affected or likely to be affected with the lesions. The retinoid is applied in a dermatologically acceptable vehicle, such as a cream base, preferably in a concentration of about 0.025 to 0.1 weight percent in the case of tretinoin, generally by daily application. When applied in the striae rubrae stage, the retinoid prevents or reduces the formation of striae albae. When applied in the striae albae stage, the scars become less noticeable, less wrinkled, and softer, though the lesions do not disappear altogether. When applied early in pregnancy before any clinical change, stretch marks may be almost completely prevented.

DETAILED DESCRIPTION OF THE PREFERRED EMBODIMENTS

The retinoid, preferably retinoic acid, also referred to as Vitamin A acid, and more particularly the all-trans isomer of retinoic acid, also known as tretinoin, is applied topically to striae distensae lesions according to the present invention. The topical application may be by spreading on with the fingers or by use of a suitable applicator such as a cotton swab.

Retinoids have been defined narrowly as comprising simply vitamin A (retinol) and its derivatives such as vitamin A aldehyde (retinal), vitamin A acid (retinoic acid), comprising the so called natural retinoids. However, subsequent research has resulted in a much larger class of chemical compounds that are termed retinoids due to their biological similarity to vitamin A and its derivatives. Compounds useful in the present invention include all natural and/or synthetic analoguss of vitamin A or retinol-like compounds which possess the biological activity of vitamin A in the skin, particularly the prevention and reduction in size of striae distensae lesions, among other effects. Accordingly, as used herein for purposes of the present invention, the term "retinoid" will be understood to include any of the foregoing compounds. Examples of suitable retinoids for use in the present invention are set forth in Table I, although it will be understood that the invention is not limited thereto.

TABLE I

Chemical, Common and/or Commercial Name

Isotretinoin 13-cis-retinoic acid ACCUTANE
Etretinate TEGISON (all-E)-9-(4-methoxy-2,3,6-trimethylphenyl)- 3,7-dimethyl-2,4,6,8-nonatetraenoic acid ethyl ester Etretin (all-E)-9-(4-methoxy-2,3,6,-trimethylphenyl)- 3,7-dimethyl-2,4,6,8,-nonatetraenoic acid Motretinide N-ethyl-9-(4-methoxy-2,3,6-trimethylphenyl)- 3,7-dimethyl-2,4,6,8-nonatetraenamide (E,E)-9-(2,6-dichloro-4-methoxy- 3-methylphenyl)3,7-dimethyl-2,4,6,8-nonatetraenoic acid ethyl ester 7,8-didehydroretinoic acid (E,E)-4-[2-methyl-4-(2,6,6-trimethyl- 1-cyclohexen-1-yl)- 1,3-butadienyl] benzoic acid (E)-4-[4-methyl-6-(2,6,6-trimethyl- 1-cyclohexen-1-yl)-1,3, 5-hexatrienyl] benzoic acid (all-E) -3,7-dimethyl-9- (3-thienyl)- 2,4,6,8-nonatetraenoic acid (E,E,E)-3-methyl-7-(5,6,7,8-tetrahydro- 5,5,8,8-tetramethyl-2-naphthalenyl)-2,4,6-octatrienoic acid (E)-6-[2-(2,6,6-trimethyl-l-chclohexen- 1-yl)ethenyl]-2-naphthalenecarboxylic acid (E,E,E)-7-(2,3-dihydro-1,1,3,3-tetramethyl- 1H-inden-5-yl)-3-methyl-2,4,6-octatrienoic acid (E)-4-(2,3-dihydro-1,1,3,3,-tetramethyl-1 H-inden-5-yl)-1-propenyl] benzoic acid TTNPB (E)-4-[2-(5,6,7,8-tetrahydro- 5,5,8,8-tetramethyl-2-naphthalenyl-1-propenyl] benzoic acid (E)-4-[2-(5,6,7,8-tetrahydro-3-methyl- 5,5,8,8-tetramethyl-2-naphthalenyl)-1-propenyl] benzoic acid (E)-1,2,3,4-tetrahydro-1,1,4,4-tetramethyl-6-( 1-methyl-2-phenylethyl) naphthalene 6-(1,2,3,4-tetrahydro-1,1,4,4-tetramethyl- 6-naphthyl)-2-naphthalenecarboxylic acid (E)-6-[2-[4-(ethylsulfonyl)phenyl- 1-methylethenyl]-1,2,3, 4-tetrahydro- 1,1,4,4-tetramethylnaphthalene 4-[(5,6,7,8-tetrahydro-5,5,8,8-tetramethyl- 2-naphthalenyl-)ethynyl] benzoic acid (E)-2-(1,1,4,4-tetramethyl- 1,2,3,4-tetrahydronaphth-7-yl-[4-tetrazol- 5-yl)phenyl]-1-propene (E)-4-[2-(5,6,7,8,-tetrahydro-7-hydroxy- 5,5,8,8-tetramethyl-2-naphthalenyl)-1-propenyl] benzyl alcohol AM-80 2-(4-Carboxybenzamido)-5,6,7,8-tetrahydro- 5,5,8, 8-tetramethylnaphthalene AM-580 2-[N-4-(Carboxyphenyl)carbamoyl]- 5,6,7,8-tetrahydro-5,5,8,8-tetramethylnaphthalene CH-55 1-[3,5-(Di-tert-butyl)benzoyl]-2-( 4Carboxyphenyl)ethene TTNT 2-(5,6,7,8-tetrahydro-5,5,8,8-tetramethyl- 2-naphthyl)-6-benzo(b) thiophene carboxylic acid TTNF 2-(5,6,7,8-tetrahydro-5,5,8,8-tetramethyl- 2-naphthyl)-6-benzo(b) furancarboxylic acid TTNI 2-(5,6,7,8-tetrahydro-5,5,8,8-tetramethyl- 2-naphthyl)-6-indolecarboxylic acid TTNN 2-(5,6,7,8-tetrahydro-5,5,8,8-tetramethyl- 2-naphthyl)-6-naphthalene carboxylic acid p-(5,6,7,8-tetrahydro-5,5,8,8-tetramethyl- 2-anthracenyl) benzoic acid Esters or amides of 13-trans retinoic acid or 13-cis retinoic acid wherein the —OH group of the carboxylic acid (—COOH) group is substituted by —OR$^1$ or —NR$^2$R$^3$ wherein R$^1$ R$^2$ and R$^3$ are such that these esters or amides can be converted to 13-trans retinoic acid or 13-cis retinoic acid through hydrolysis, metabolism, cleavage, etc.

Also encompassed within the term "retinoid" are geometric and stereoisomers of the retinoids. While the specific examples below use tretinoin (all-trans retinoic acid), isotretinoin (13-cis-retinoic acid) may also be used, although somewhat higher concentrations are needed to obtain equivalent results.

Retinoids may be formulated in bland, moisturizing bases, such as creams or ointments, usually in low concentrations, although higher concentrations may be used for darker skins. The retinoid should preferably be applied in an amount which is not excessively irritating to the skin. Other non-toxic, dermatologically acceptable vehicles or carriers in which retinoids are stable will be evident to those of ordinary skill in the art. In general, emollient or lubricating vehicles, such as oleaginous substances, which help hydrate the skin are preferred. As used herein, the term "emollient" will be understood to refer to the non-irritating character of the composition as a whole. That is, the nature of the vehicle and amount of retinoid therein should be selected so as to provide a sub-irritating dose for topical application. Volatile vehicles which dry or otherwise harm the skin, such as alcohol and acetone, should be avoided.

An ointment base (without water) is preferred in the winter and in subjects with very dry skin. Examples of suitable ointment bases are petrolatum, petroldrum plus volatile silicones, lanolin, and water in oil emulsions, such as Eucerin (Beiersdorf).

In warm weather and often for younger persons, oil in water emulsion (cream) bases, are preferred. Examples of suitable cream bases are Nivea Cream (Beiersdorf), cold cream (USP), Purpose Cream (Johnson & Johnson), hydrophilic ointment (USP), and Lubriderm (Warner-Lambert).

Some retinoids are mild irritants and may cause redness and scaling, which may be accompanied by some tenderness and tightness. These reactions are transient and quickly disappear when the applications are stopped. However, the skin rapidly accommodates, and even when retinoids are applied excessively to produce visible inflammation, the reaction slowly disappears leaving no permanent sequellae. Systemic side reactions are unknown and are not to be expected from such low concentrations according to the present invention. Selection of an appropriate emollient vehicle will more readily allow the use of a highly effective but sub-irritating does of the retinoid.

Retinoic acid may be applied in any dermatologically acceptable vehicle such as a gel or a cream base. Retinoic acid in a cream base is available commercially for the treatment of ache from Johnson & Johnson under the trademark RETIN-A, which is available in concentrations ranging from 0,025 to 0.1 weight percent. Gel bases of RETIN-A are also available. Other suitable formulations will be apparent to those skilled in the art based upon the present disclosure.

For purposes of the present invention where the retinoid is retinoic acid, the retinoic acid is generally applied in a concentration of about 0.025 to 0.1 weight percent of the total composition, and preferably about 0.25 to 0.1 weight percent of the composition. Such concentrations are too low to cause birth defects (teratogenicity). Also, concentrations of 0.1 percent or less are insufficient to cause any side effects other than some minor early irritation to which the skin gradually accommodates. No systemic effects have been reported in the treatment of many millions of ache sufferers.

Generally, the topical applications are made once daily, although twice daily or thrice weekly applications may prove beneficial or satisfactory in some cases. Clinically significant improvement is usually seen after 4 to 5 months of daily treatment. The width and depth of stretch marks is greatly reduced. Tenderness and redness are ameliorated.

For best results, the topical applications of retinoid are started in the early red stage (striae rubrae) in the first few months after conception. When started at this stage, not only will the lesions become narrower, shallower and much less noticeable, but permanent scarring will be largely prevented in at least about half of the patients treated. The prophylactic strategy of beginning the treatment of the invention in early pregnancy yields optimal results. The treatment should continue at least until birth, and possibly for another few months after birth, although the benefits of post-natal therapy are still being investigated.

When the topical retinoid treatments of the present invention are not started until the lesions have reached the striae albae stage, it is still possible to soften the scars, reduce their depth, and improve the texture of the skin with the topical applications. In these cases, the dreaded and embarrassing stretch marks can be significantly reduced in size so that they are less noticeable. Old, long-standing striae albae lesions improve only slightly.

While applicant does not wish to be bound by any particular theory, it is believed that the mechanism of action of retinoids in preventing and reducing the size of stride distensae is due to two actions: (1) suppression of inflammation present in stride rubrae (we have shown that there is an intense inflammatory reaction in biopsies from stride rubrae) and (2) stimulation of new collagen formation resulting in shallower, softer scars in both stride rubrae and stride albae.

The invention will now be illustrated in further detail by reference to the following specific, non-limiting examples.

EXPERIMENTAL EXAMPLES

Over forty women with striae distensae were treated according to the present invention. The lesions on one side of the abdomen were treated with 0.05 to 0.1 percent RETIN-A cream, generally once daily, while Nivea Cream alone was applied to the other side of the abdomen as a control. Most of the forty test subjects were 3 to 5 months pregnant, showing stride rubrae. The remainder had stride albae of varying duration, usually not greater than 5 years. Tretinoin was applied once daily at the start of therapy. This was sometimes increased to twice daily in those who experienced little irritation.

In the cases where treatment was begun in the stride rubrae stage, about half were greatly improved in comparison to the control. In three cases where treatment was started in the first few weeks of pregnancy before any evidence of striae distensae, the suppression of striae on the treated side was impressive (almost complete) in two of the cases. Where the treatment did not begin until the striae albae stage, about one third showed clinically significant improvement after 4 to 5 months of daily treatment. The improved women were impressed with the results. The only side effects have been some early irritation, which was temporary.

In the four cases which were biopsied, the histology showed nearly normal skin, with good collagen bundles, on the side treated with RETIN-A. The control side showed fine fibers, tightly packed in parallel array, typical of a scar.

The present invention may be embodied in other specific forms without departing from the spirit or essential attributed thereof, and accordingly, reference should be made to the appended claims, rather than to the foregoing specification as indicating the scope of the invention.

I claim:

1. A method of eliminating or reducing the size of striae distensae lesions comprising applying topically to the area of the skin affected with said lesions a composition comprising an amount of a retinoid effective to reduce or eliminate said lesions.

2. A method according to claim 1 wherein said composition is applied about once daily to said area.

3. A method according to claim 1 wherein said retinoid is applied in an emollient vehicle.

4. A method according to claim 1, wherein said composition is applied in a dematologically acceptable vehicle containing said retinoid at a concentration equivalent to about 0.025 to 0.1 weight percent retinoic acid.

5. A method according to claim 4 wherein said vehicle is a cream or gel base.

6. A method according to claim 1 wherein said composition is applied to the skin in the striae rubrae stage of the lesions to reduce the size of the lesions and prevent the formation of striae albae.

7. A method according to claim 1 wherein said composition is applied to the skin in the striae albae stage of the lesions to reduce the size of the lesions.

8. A method of preventing the formation of significant striae distensae of the abdomen comprising applying topically to the skin of the abdomen an effective amount of a retinoid during early pregnancy prior to clinical appearance of lesions.

* * * * *